United States Patent
Lee et al.

(10) Patent No.: US 12,343,569 B2
(45) Date of Patent: Jul. 1, 2025

(54) METHOD OF RADIATING WAVE ENERGY AVAILABLE FOR UNMANNED AUTOMATIC OPERATION AND APPARATUSES FOR PERFORMING THE SAME

(71) Applicant: ELECTRONICS AND TELECOMMUNICATIONS RESEARCH INSTITUTE, Daejeon (KR)

(72) Inventors: Kwang Jae Lee, Daejeon (KR); Soon Ik Jeon, Daejeon (KR); Woo Jin Byun, Daejeon (KR); In Kui Cho, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1108 days.

(21) Appl. No.: 17/235,248

(22) Filed: Apr. 20, 2021

(65) Prior Publication Data

US 2021/0322793 A1  Oct. 21, 2021

(30) Foreign Application Priority Data

Apr. 21, 2020  (KR) .................. 10-2020-0047894

(51) Int. Cl.
*A61N 7/02* (2006.01)
*A61N 1/40* (2006.01)
*A61N 5/02* (2006.01)
*A61N 7/00* (2006.01)

(52) U.S. Cl.
CPC .............. *A61N 7/02* (2013.01); *A61N 1/403* (2013.01); *A61N 5/025* (2013.01); *A61N 2007/0004* (2013.01)

(58) Field of Classification Search
CPC ..................................................... A61N 1/403
See application file for complete search history.

(56) References Cited

U.S. PATENT DOCUMENTS

| | | | |
|---|---|---|---|
| 2011/0130656 A1* | 6/2011 | Son | A61B 5/0507 600/430 |
| 2014/0012063 A1 | 1/2014 | Turner et al. | |
| 2018/0250522 A1 | 9/2018 | Jeon et al. | |
| 2018/0264281 A1* | 9/2018 | Kim | A61N 5/025 |
| 2019/0111275 A1 | 4/2019 | Jeon et al. | |

FOREIGN PATENT DOCUMENTS

| | | |
|---|---|---|
| KR | 10-2016-0118919 A | 10/2016 |
| KR | 20190042431 A | 4/2019 |
| KR | 10-2020-0007312 A | 1/2020 |

* cited by examiner

*Primary Examiner* — Kaitlyn E Smith
(74) *Attorney, Agent, or Firm* — Rabin & Berdo, P.C.

(57) ABSTRACT

Disclosed are a method of radiating wave energy available for unmanned automatic operation and apparatuses for performing the same. The method includes obtaining a dielectric characteristic of a object by performing a reconstruction calculation based on a scattered signal that is scattered from the object and pre-measured information on the object, determining a wave radiation parameter for adjusting energy of a wave to be radiated to a lesion of the object by performing a characteristic analysis operation based on the dielectric characteristic, and determining the energy of the wave to be high-power energy based on the wave radiation parameter.

19 Claims, 4 Drawing Sheets

METHOD OF RADIATING WAVE ENERGY AVAILABLE FOR UNMANNED AUTOMATIC OPERATION AND APPARATUSES FOR PERFORMING THE SAME

CROSS-REFERENCE TO RELATED APPLICATION(S)

This application claims the benefit of Korean Patent Application No. 10-2020-0047894, filed on Apr. 21, 2020, in the Korean Intellectual Property Office, the disclosure of which is incorporated herein by reference.

BACKGROUND

1. Field of the Invention

One or more example embodiments relate to a method of radiating wave energy available for unmanned automatic operation and apparatuses for performing the same.

2. Description of the Related Art

In the aging society, senile disease treatments may include treatments of intractable diseases including cancer, and treatments of degenerative musculoskeletal diseases. Such senile disease treatments are performed mainly by incision surgery. However, in recent years, non-invasive energy treatments are getting popular as alternative treatments because patients experience pain, physical burden, and side effects such as relapses. Non-invasive energy treatments radiate high-density energy from the outside of a living body to a lesion inside the living body such that the energy is converted into heat to treat with the heat.

Wave energy used for such non-invasive energy treatments is being studied as an excellent non-invasive technique. Wave energy is less harmful than radiation and may be applied to bones and air structures without limitation, like ultrasonic waves.

Non-invasive energy treatments are performed without incision and thus, need to radiate wave energy accurately to a target lesion. However, the currently commercialized techniques merely radiate wave energy based on the imperfect experience of wave living body propagation operations and clinical tests and thus, have difficulty in precise investigation operation.

The current ultrasonic thermal treatments widely used for musculoskeletal diseases have unintended side effects, such as high fever or burns, caused by standing waves generated by the skeleton, and thus rubbing procedures are performed under the supervision of medical specialists. However, the rubbing procedures exhibit low efficiency in transferring energy intensively to a site of a lesion, and there is an issue of the manpower load of medical specialists.

SUMMARY

An aspect provides technology for radiating wave energy to a object more precisely and efficiently and performing an automatic operation in the order of program configuration.

Through this, example embodiments may provide a thermal treatment system available for unmanned automatic operation.

However, the technical aspects are not limited to the aforementioned aspects, and other technical aspects may be present.

According to an aspect, there is provided a method of radiating wave energy available for unmanned automatic operation, the method including obtaining a dielectric characteristic of a object by performing a reconstruction calculation based on a scattered signal that is scattered from the object and pre-measured information on the object, determining a wave radiation parameter for adjusting energy of a wave to be radiated to a lesion of the object by performing a characteristic analysis operation based on the dielectric characteristic, and determining the energy of the wave to be high-power energy based on the wave radiation parameter.

The method may further include radiating the wave whose energy is adjusted to the high-power energy to the lesion based on the wave radiation parameter.

The dielectric characteristic may include a first dielectric characteristic indicating rough information on the external figure and musculoskeletal system of the object and a second dielectric characteristic indicating detailed information on the internal tissues of the object.

The first dielectric characteristic may include a rough dielectric characteristic of the object, and the rough dielectric characteristic of the object may be related to the shape and size of the external figure of the object and the musculoskeletal system including the muscles and bones of the object.

The second dielectric characteristic may include a detailed dielectric characteristic of the object, and the detailed dielectric characteristic may be related to the distribution of the internal muscles, fat, nerves, and vessels of the object, and the structure and positions of the skeleton and bones.

The pre-measured information may be the site of the lesion, the position of the lesion, the shape, size, and diameter with respect to the external figure of the object, the distribution of the internal muscles of the object, and anatomical information on the skeleton and bone structure.

The obtaining may include obtaining the scattered signal that is scattered from the object by radiating a wave of low-power energy to the object, obtaining the first dielectric characteristic based on the scattered signal and the pre-measured information, and obtaining the second dielectric characteristic based on the pre-measured information and the first dielectric characteristic.

The determining of the wave radiation parameter may include determining a channel-wise wave radiation parameter for the wave based on the first dielectric characteristic and the second dielectric characteristic.

The determining of the energy of the wave to be high-power energy may include outputting a wave of low-power energy based on the channel-wise wave radiation parameter, amplifying the wave of the low-power energy to a wave of the high-power energy, and determining the wave of the high-power energy as the wave to be radiated to the lesion.

According to another aspect, there is provided an apparatus for radiating wave energy available for unmanned automatic operation, the apparatus including an antenna, and a controller configured to obtain a dielectric characteristic of a object by performing a reconstruction calculation based on a scattered signal that is scattered through the antenna from the object and pre-measured information on the object, to determine a wave radiation parameter for adjusting energy of a wave to be radiated to a lesion of the object by performing a characteristic analysis operation based on the dielectric characteristic, and to determine the energy of the wave to be high-power energy based on the wave radiation parameter.

The controller may be further configured to radiate the wave whose energy is adjusted to the high-power energy to the lesion based on the wave radiation parameter.

The dielectric characteristic may include a first dielectric characteristic indicating rough information on the external figure and musculoskeletal system of the object and a second dielectric characteristic indicating detailed information on the internal tissues of the object.

The first dielectric characteristic may be a rough dielectric characteristic related to the shape and size of the external figure of the object and the musculoskeletal system including the muscles and bones of the object.

The second dielectric characteristic may be a detailed dielectric characteristic related to the distribution of the internal muscles, fat, nerves, and vessels of the object, and the structure and positions of the skeleton and bones.

The pre-measured information may be the site of the lesion, the position of the lesion, the shape, size, and diameter with respect to the external figure of the object, the distribution of the internal muscles of the object, and anatomical information on the skeleton and bone structure.

The controller may be further configured to obtain the scattered signal that is scattered from the object by radiating a wave of low-power energy to the object, to obtain the first dielectric characteristic based on the scattered signal and the pre-measured information, and to obtain the second dielectric characteristic based on the pre-measured information and the first dielectric characteristic.

The controller may be further configured to determine a channel-wise wave radiation parameter for the wave based on the first dielectric characteristic and the second dielectric characteristic.

The controller may be further configured to output a wave of low-power energy based on the channel-wise wave radiation parameter, to amplify the wave of the low-power energy to a wave of the high-power energy, and to determine the wave of the high-power energy as the wave to be radiated to the lesion.

The controller may be further configured to determine the number of wave radiation channels through which the wave is to be radiated, and to radiate the wave whose energy is adjusted to the high-power energy based on the determined number of wave radiation channels.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Hereinafter, example embodiments will be described in detail with reference to the accompanying drawings. However, various alterations and modifications may be made to the example embodiments. Here, the example embodiments are not construed as limited to the disclosure. The example embodiments should be understood to include all changes, equivalents, and replacements within the idea and the technical scope of the disclosure.

The terminology used herein is for the purpose of describing particular example embodiments only and is not to be limiting of the example embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous analysis of the present disclosure.

Also, in the description of the components, terms such as first, second, A, B, (a), (b) or the like may be used herein when describing components of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 1:
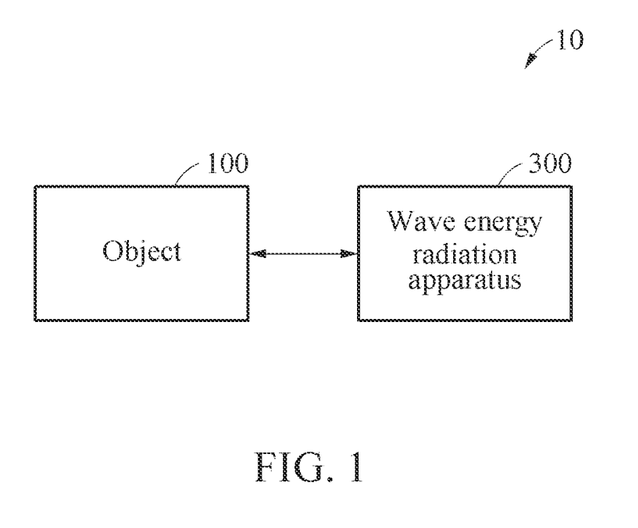
FIG. 1 is a block diagram illustrating a wave energy radiation system according to an example embodiment.

FIG. 1 is a block diagram illustrating a wave energy radiation system according to an example embodiment.

A wave energy radiation system 10 may be a wave energy treatment system that is available for unmanned automatic operation.

The wave energy radiation system 10 includes a object 100 and a wave energy radiation apparatus 300.

The object 100 may be a body part including a lesion requiring treatment. The body part may include various body parts such as the knees, neck, waist, and head. The lesion of the object 100 may require energy treatment using waves. The energy of a wave may be converted into heat inside a living body.

The wave energy radiation apparatus 300 may obtain a dielectric characteristic of the object 100 in real time, and radiate a wave (or energy of a wave) determined based on the dielectric characteristic to the lesion of the object 100.

Through this, the wave energy radiation apparatus 300 may discern a wave environment of the object 100 in advance using a real-time fast wave calculating method of determining the energy of a wave, build a wave procedure plan based on the wave environment, and perform a wave procedure based on the wave procedure plan. In this example, the wave energy radiation apparatus 300 may perform, through a program in real time and automatically, the process of discerning the wave environment in advance, building the wave procedure plan, and performing the wave procedure.

The wave energy radiation apparatus 300 may more precisely and efficiently radiate wave energy to the object 100 through real-time and automatic operation, thereby providing an energy treatment technique (or treatment and system) available for unmanned automatic operation without the direct procedure by existing medical specialists.

Figure 2:
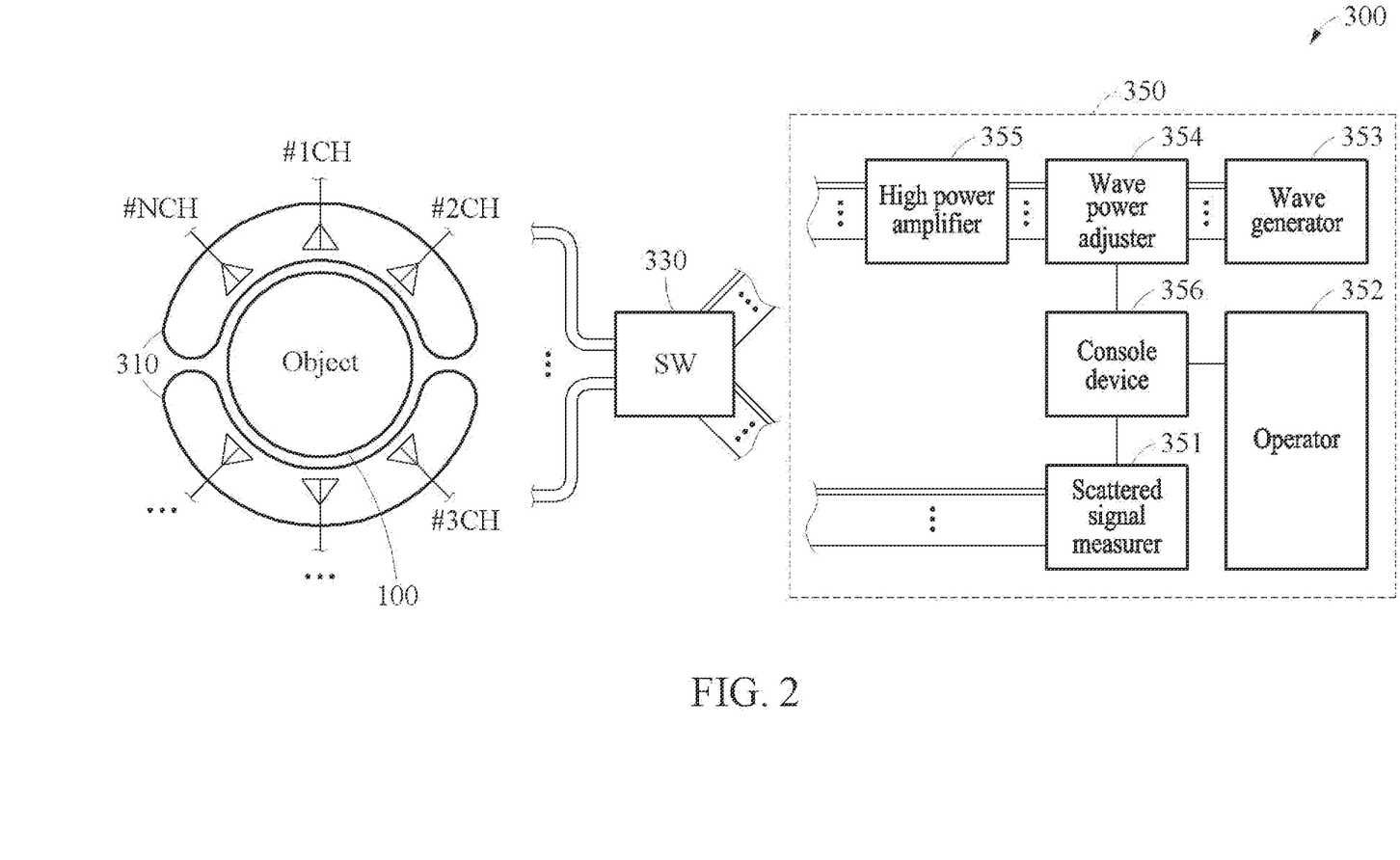
FIG. 2 is a block diagram illustrating a wave energy radiation apparatus shown in FIG. 1.

FIG. 2 is a block diagram illustrating a wave energy radiation apparatus shown in FIG. 1.

The wave energy radiation apparatus 300 includes an antenna module 310, a switch module 330, and a controller 350.

The antenna module 310 may include an antenna array element and an interface. The antenna array element may include antennas. The antennas may be positioned around the object 100 to enclose the object 100. The interface may enclose the object 100 with a pouch and pads so as to smoothly attach to the object 100 for better wave matching.

The antenna module 310 may transmit and receive a wave for each antenna (or for each channel). For example, to obtain scattering information of the object 100, the antennas may radiate low-power waves to the lesion of the object 100 and receive scattered signals that are scattered from the object 100 by the low-power waves. The low-power waves may be weak wave signals that are output with low power (or low-power energy).

Further, the antennas may radiate high-power waves to the lesion of the object 100 to treat the lesion of the object 100. The high-power waves may be wave signals that are output with high power (or high-power energy).

The switch module 330 may validate one of a wave radiation planning mode and a wave radiation procedure mode by switching between the wave radiation planning mode and the wave radiation procedure mode.

For example, in the wave radiation planning mode, the switch module 330 may be connected to a scattered signal measurer 351 to connect the antenna module 310 and the scattered signal measurer 351. The wave radiation planning mode may be the process of extracting (or determining) a wave radiation parameter of a wave to be radiated to the lesion of the object 100 based on the dielectric characteristic of the object 100 and determining the energy of the wave to be high-power energy to treat the lesion of the object 100.

In the wave radiation procedure mode, the switch module 330 may be connected to a high power amplifier 355 to connect the antenna module 310 and the high power amplifier 355. The wave radiation procedure mode may be the process of treating the lesion by radiating the high-power wave energy determined through the wave radiation planning mode to the lesion.

The controller 350 may include the scattered signal measurer 351, an operator 352, a wave generator 353, a wave power adjuster 354, the high power amplifier 355, and a console device 356. The scattered signal measurer 351, the operator 352, the wave generator 353, the wave power adjuster 354, the high power amplifier 355, and the console device 356 may be implemented by modules.

The scattered signal measurer 351 may obtain the scattering information of the object 100 based on the scattered signal received by transmitting and receiving signals through the antenna module 310. The scattered signal measurer 351 may transmit the obtained scattering information to the operator 352. In this example, the scattered signal measurer 351 may transmit the scattering information in the form of data (or a scattering information matrix) to the operator 352. The scattering information may be unique scattering information according to the internal structure of the object 100.

For example, biological tissues have different electromagnetic characteristics (or scattering characteristics) according to different tissue structures (or physical distribution of different tissue structures). An electromagnetic characteristic may be a dielectric characteristic of biological tissue, for example, the permittivity and conductivity of the biological tissue. Biological tissues to which waves are radiated emit scattered signals determined according to the physical distribution of different tissue structures. In this example, the scattered signals include unique scattering information according to the internal structures of the biological tissues. The scattering information may be the sizes, phase values, and waveforms of the scattered signals. Thus, the scattering information of the object 100 may be the sizes, phase values, and waveforms of the scattered signals determined according to the physical distribution (for example, the size, position, and shape) of the internal structure (for example, the bones, organs, muscles, and fat) of the object 100.

The operator 352 may obtain the dielectric characteristic of the object 100 by reconstructing the scattering information to a physical distribution (or image) based on the obtained scattering information and pre-measured information of the object 100, and determine the wave radiation parameter based on the dielectric characteristic of the object 100 which is a reconstruction result. In this example, the pre-measured information is additional information obtained in advance through measurement and may be rough information related to the object 100 and the lesion of the object 100. The pre-measured information may be information on the site of the lesion of the object 100, the position of the lesion, the shape, size, and diameter with respect to the external figure of the object 100, and the distribution of the internal muscles of the object 100, and anatomical information on the skeleton and bone structure. The anatomical information may be information specific to the structure of muscles and bones. The dielectric characteristic of the object 100 is an electromagnetic characteristic of the object 100 and may include a complex dielectric value of the object 100 and a quantitative value determining the electromagnetic phenomenon. The complex dielectric value of the object 100 may be a physical value having a quantitative value, for example, the electrical permittivity and electrical conductivity of the object 100. The quantitative value determining the electromagnetic phenomenon of the object 100 may be an electric field value and a value of the Green's function.

The wave generator 353 may generate the wave to be radiated to the object 100.

The wave power adjuster 354 may output low-power wave energy by adjusting the energy of the wave generated by the wave generator 353 to low-power energy based on the wave radiation parameter determined by the operator 352. In this example, the wave power adjuster 354 may adjust the energy of the wave for each channel of the antenna module 310.

The high power amplifier 355 may output high-power wave energy by amplifying the low-power wave energy output from the wave power adjuster 354 to high-power energy.

The console device 356 is a basic operator that performs electrical and mechanical timing control of the modules included in the controller 350, and may be a detailed operation control and operation program operator.

The controller 350 may perform a wave radiation planning operation and an automatically operable wave energy radiation procedure operation (or automatically operable wave energy treatment procedure operation) through the modules included in the controller 350. The wave radiation planning operation will be described in detail with reference to FIG. 3, and the automatically operable wave energy radiation procedure operation will be described in detail with reference to FIG. 4.

Figure 3:
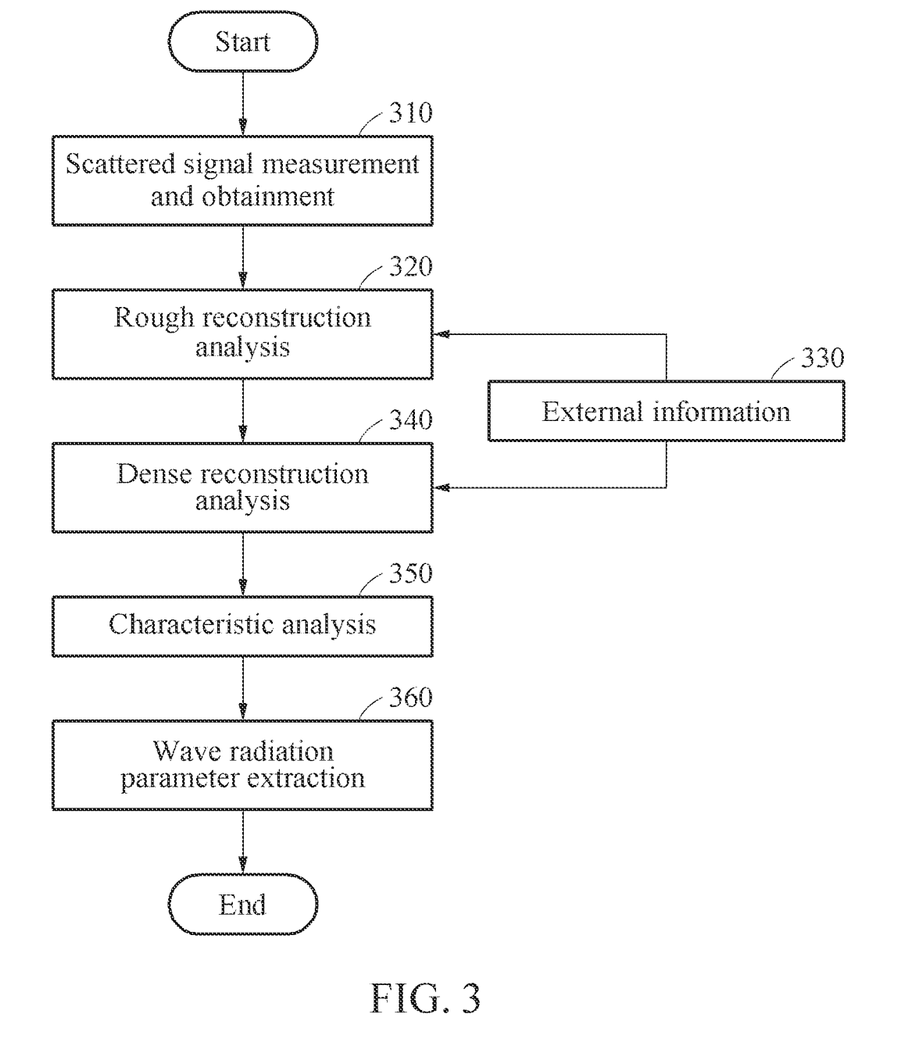
FIG. 3 is a flowchart illustrating a wave radiation planning operation of a wave energy radiation apparatus.

FIG. 3 is a flowchart illustrating a wave radiation planning operation of a wave energy radiation apparatus.

The controller 350 may perform a wave radiation planning operation through a real-time fast propagation operation process performed by the operator 352.

For example, by performing the real-time fast propagation operation process through the operator 352, the controller 350 may determine a wave radiation parameter of a wave to be radiated to the lesion of the object 100 and to determine the energy of the wave to be radiated to the lesion to be high-power energy according to the wave radiation parameter. The real-time fast propagation operation process may include a rough reconstruction analysis operation, a dense reconstruction analysis operation, and a characteristic analysis operation. The rough reconstruction analysis operation and the dense reconstruction analysis operation may be for obtaining the dielectric characteristic of the object 100, and the characteristic analysis operation may be for determining the wave radiation parameter of the wave to be radiated to the object 100. The dielectric characteristic of the object 100 may include a first dielectric characteristic indicating rough information on the external figure and musculoskeletal system of the object 100, and a second dielectric characteristic indicating detailed information on the internal tissues of the object 100. The first dielectric characteristic may be a rough dielectric characteristic related to the shape and size of the external figure of the object 100 and the musculoskeletal system such as the muscles and bones of the object 100. The second dielectric characteristic may be a detailed dielectric characteristic related to the distribution of the internal muscles, fat, nerves, and vessels of the object 100, and the structure and positions of the skeleton and bones.

For example, the operator 352 may obtain the rough dielectric characteristic of the object 100 by performing rough reconstruction analysis.

When the object 100 is loaded in the antenna module 310, the switch module 330 may switch the mode of the wave energy radiation apparatus 300 to a wave radiation planning mode. When the mode of the wave energy radiation apparatus 300 is switched to the wave radiation planning mode, the controller 350 may radiate low-power wave energy to the object 100 through the antenna module 310 and the scattered signal measurer 351.

In operation 310, the controller 350 may obtain a scattered signal that is scattered from the object 100 through the scattered signal measurer 351, and obtain scattering information based on the scattered signal. In this example, the number of antenna elements in the antenna module 310 may be equivalent to the number of channels. The quality of scattering information and the wave energy radiation efficiency may be determined according to the number of channels.

For example, to obtain the scattering information, the scattered signal measurer 351 may be connected to the antenna module 310 through N lines, thereby applying a transmission signal through a first channel and receiving scattered signals that are scattered from the object 100 through the remaining channels (second to nth channel). In the manner described above, the scattered signal measurer 351 may sequentially transmit a transmission signal through any one of the second to nth channels and receive scattered signals for all the channels. In this example, the console device 356 may switch in a predetermined order by adjusting the scattered signal measurer 351, such that the scattered signal for each channel may be obtained. For example, the console device 356 may manage a detailed operation to obtain a predetermined channel signal, such as, to obtain a first channel signal.

The scattered signal measurer 351 may obtain final scattering information based on the scattered signals for all the channels and transmit the obtained final scattering information to the operator 352.

In operation 320, the operator 352 may obtain the first dielectric characteristic that is the rough dielectric characteristic of the object, by performing the rough reconstruction analysis (or rough reconstruction analysis process) using the obtained scattering information. The first dielectric characteristic may be a rough physical distribution result (or dielectric characteristic distribution) for the external figure, muscles, and bones of the object 100. The physical distribution result may be rough images of the external figure, muscles, and bones of the object 100, and indicate various dielectric characteristics related to the external figure of the object 100 such as the shape and size of the object 100 and dielectric characteristics related to the positions, shapes, and sizes of the muscles and bones of the object 100.

The rough reconstruction analysis may be configured as a computer program for numerically interpreting electromagnetic phenomena. The computer program may be an electromagnetic phenomena numerical analysis program, and may reconstruct the scattering information to a physical distribution for the object 100 by performing back-scattering reconstruction and obtain the first dielectric characteristic of the object 100 based on the physical distribution. Back-scattering reconstruction may be the process of obtaining an internal characteristic function M through an input signal X and an output signal Y (for example, Y=M*X). The internal characteristic function M may reflect the dielectric characteristic.

The electromagnetic phenomena numerical analysis program may require condition values such as the initial value and boundary condition of the dielectric characteristic to reconstruct the dielectric characteristic result based on the scattering information. The boundary condition may be an additional conditional expression for calculating a complex electromagnetic phenomenon occurring outside without complex calculation by setting the phenomenon with a simple condition. Although the outside of the object 100 is not an object of interest, the electromagnetic field outside the object 100 may have effects and thus, may not be ignored.

If a condition value more similar to the actuality is input, the electromagnetic phenomena numerical analysis may derive results more quickly and precisely. For example, the back-scattering reconstruction process may be the process of obtaining the final M by repeatedly updating with a value close to ground truth by setting the value of M to a predetermined initial value M0. The value close to ground truth may be a value with an error (a) close to zero. The back-scattering reconstruction process reflecting the initial value may be Y≈M0*X, where Y=M0*X+a.

To derive the results more quickly and precisely as described above, in operation 330, the operator 352 may obtain a rough dielectric characteristic of the object based on pre-measured information on the object 100 as well as the scattered signal. The pre-measured information may be a condition value for reconstructing the dielectric characteristic result, and may be external information on the object 100 such as the size and part information of the object 100. The external information on the object 100 may be the site of the lesion previously measured from the object 100, the position of the lesion, the diameter (or outer diameter) of the lesion, and the external figure, size, and diameter of the object 100. If the object 100 requires knee arthritis thermal treatment, the pre-measured information may be the position and diameter of the knee of the object 100, and the diameter of the knee joint. If the object is a knee and the diameter of the knee is set, rough reconstruction analysis may be performed on the outermost of the object 100 by inputting the values of skin and fat as simple boundary conditions.

Since the knee joints of many people are in practically similar structures, complementary information such as the anatomical structure of the knee joint may apply to various patients requiring treatment.

When the pre-measured information is input as the initial value and the boundary condition value and used for the rough reconstruction analysis, the time required for obtaining the dielectric characteristic distribution result may be reduced, and the quality of the dielectric characteristic distribution result may improve.

In operation 340, after the rough reconstruction analysis is performed the operator 352 may obtain a detailed dielectric characteristic of the object 100 by performing dense reconstruction analysis, if necessary, according to the procedure situation and accuracy. For example, the operator 352 may obtain a second dielectric characteristic, which is a detailed dielectric characteristic of the object 100, based on a first dielectric characteristic, which is a rough dielectric characteristic. The operator 352 may obtain a more detailed dielectric characteristic distribution result based on the rough dielectric characteristic, which is a rough analysis result, as an initial value and a boundary condition value. The detailed dielectric characteristic may be a detailed physical distribution result for the internal tissues of the object 100. The detailed dielectric characteristic may include various dielectric characteristics related to the internal tissues of the object 100, such as the internal muscle distribution, the skeleton, and the bone structure and positions of the object 100.

In addition, the operator 352 may reduce the time required for dense reconstruction analysis and improve the quality of results using pre-measured information of the object 100 in addition to the rough dielectric characteristic of the object, in the dense reconstruction analysis operation as well.

In operation 350, the operator 352 may perform a characteristic analysis operation using the dielectric characteristics of the object 100 obtained in the rough and dense reconstruction analysis. In operation 360, the operator 352 may determine a wave radiation parameter for the wave to be radiated to the object 100. The wave radiation parameter may include various parameters related to the wave to be radiated to the lesion of the object 100 to treat the lesion. The wave radiation parameter may be a parameter to adjust the energy and phase of the wave and include a weight of each channel of the antenna module 310. For example, in order to treat the lesion using a wave, the wave of which the energy and phase are adjusted appropriately by the antenna module 310 positioned outside the object 100 should be radiated to the lesion. The wave energy is concentrated on the lesion to which the wave is radiated. In this example, the significant parameters are the magnitude and phase for each channel of the antenna module 310, which may be referred to as wave radiation parameters. If a continuous wave is used as a treatment wave source according to an operation scheme, the wave radiation parameters may be parameters for the magnitude and phase of the continuous wave. If a pulse wave is used as a treatment wave source according to the operation scheme, the radio wave radiation parameters may be parameters for the pulse size and pulse width of the pulse wave. For example, the operator 352 may determine channel-wise wave radiation parameters for the wave to be radiated to the lesion based on the rough dielectric characteristic and the detailed dielectric characteristic of the object 100 through an electromagnetic analysis program. The operator 352 may perform a simulation for radiating efficient wave energy to a target lesion using the dielectric characteristic distribution of the object 100 as a profile through the electromagnetic analysis program for performing a characteristic analysis. In this example, the simulation may be a back-scattering analysis, and be an analysis for predicting the actual electromagnetic field by solving an electromagnetic field analysis equation using a computer. The operator 352 may output the determined channel-wise wave radiation parameters to the console device 356, and the operation of the operator 352 may be terminated.

The controller 350 may determine the energy of the wave to be radiated to the lesion of the object to treat the lesion, to be high-power energy based on the channel-wise wave radiation parameters, thereby completing (or terminating) the wave radiation planning operation for planning on radiating the wave to the lesion.

For example, the console device 356 may apply a console control signal for adjusting the weight (for example, the power magnitude and phase) of the wave power adjuster 354 to the wave power adjuster 354 to adjust the energy of the wave.

If a continuous wave is used as a treatment wave source, the console device 356 may input the magnitude and phase of power, which are the channel-wise wave radiation parameters, to the wave power adjuster 354 and adjust the power for each channel. In this example, the wave power adjuster 354 may output low power of which the weight is adjusted, and the high power amplifier 355 may output high power corresponding to the low power. The high power amplifier 355 may not require a parameter.

That is, the wave radiation parameters may be input as the channel-wise power weight for the wave power adjuster 354 and the high power amplifier 355.

If the parameters required for a first channel (CH1) are 3 W (magnitude) and 0 degrees (phase), and the parameters required for a second channel (CH2) are 10 W (magnitude) and 90 degrees (phase), the wave radiation parameters may be input as CH1(3,0) and CH2(10,90). If the input RF power of the wave power adjuster 354 is equally input to all channels as 1 mW, by the weight, CH1 may output a wave with the magnitude and phase adjusted to 3 mW and 0 degrees, and CH2 may output a wave with the magnitude and phase adjusted to 10 mW and 90 degrees. The high power amplifier 355 may amplify the power of all channels 1000 times (30 dB) and output the amplified power to each channel. For example, finally, CH1 may output a wave with the magnitude and phase adjusted to 3 W and 0 degrees, and CH2 may output a wave with the magnitude and phase adjusted to 10 W and 90 degrees.

Figure 4:
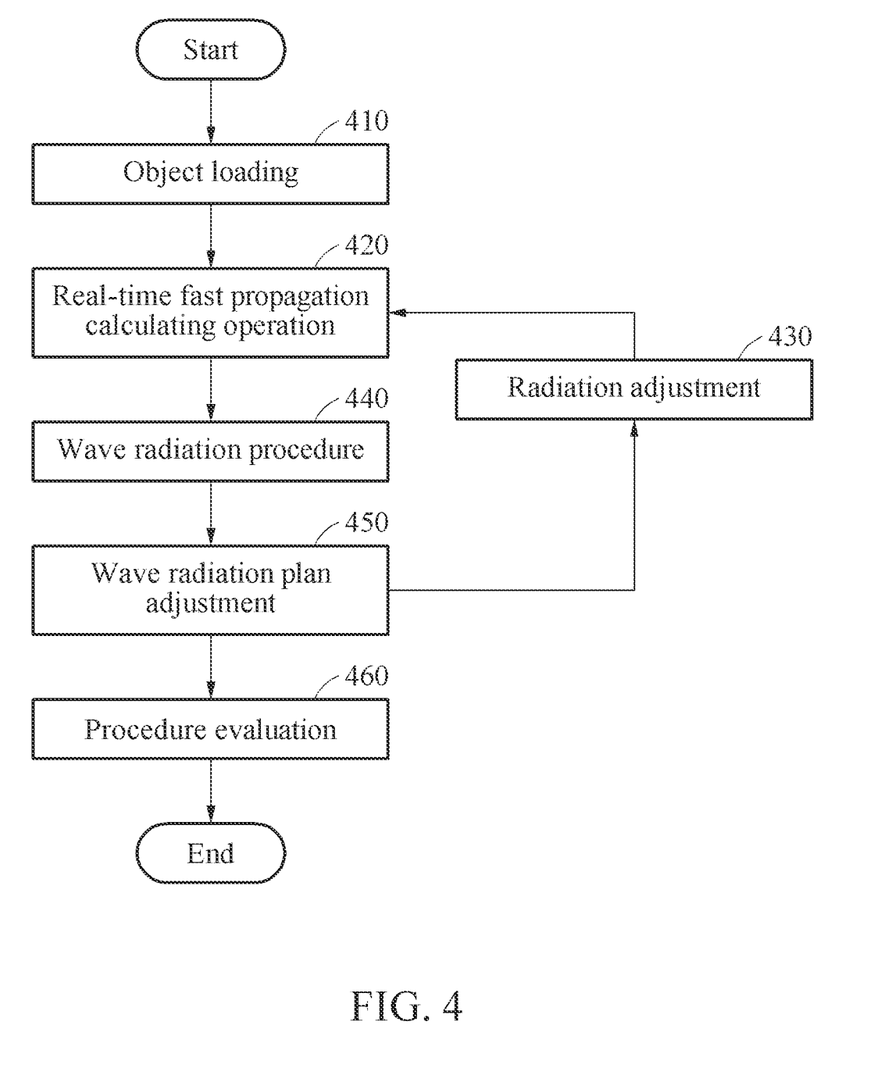
FIG. 4 is a flowchart illustrating an automatically operable wave energy radiation procedure operation of a wave energy radiation apparatus.

FIG. 4 is a flowchart illustrating an automatically operable wave energy radiation operation of a wave energy radiation apparatus.

The controller 350 may perform an automatically operable wave energy treatment radiation operation that is performed through a real-time fast propagation operation process.

For example, the controller 350 may perform the real-time fast propagation calculating operation process (operations 410 and 420) and then, perform an automatically operable wave energy treatment radiation operation.

When the object 100 is loaded in operation 410, the controller 350 may obtain scattering information from the scattered signal measurer 351 through a wave radiation planning mode of the switch module 330, and obtain a wave radiation parameter required for wave radiation planning through the real-time fast propagation calculating operation by the operator 352, in operation 420.

The controller 350 may adjust the energy of a wave to be high-power energy with an adjustment weight determined by the console device 356 based on the wave radiation parameter through switching to a wave radiation procedure mode by the switch module 330, and radiate the wave whose energy is adjusted to the high-power energy to a lesion, in operation 440.

For example, the controller 350 may adjust the energy of the wave to high-power energy according to the wave energy determined by the operator 352 through the console device 356 to treat the lesion of the object 100 and radiate the adjusted wave to the lesion of the object 100. In this example, the controller 350 may determine the number of wave radiation channels through which the high-power energy is to be radiated (or the number of antenna elements that transmit and receive energy) based on the determined high-power wave energy. The controller 350 may radiate the wave whose energy is adjusted to the high-power energy to the lesion based on the determined number of wave radiation channels.

The controller 350 may change (or adjust) the site and radiation power for the next procedure based on a programmed wave radiation plan, in operation 430 and 450, thereby re-performing the real-time fast propagation operation and repeatedly radiating waves.

For example, for efficient treatment of the object 100, the controller 350 may perform a rough reconstruction analysis operation and perform prior treatment on the lesion based on a rough wave radiation parameter determined according to the rough reconstruction analysis operation.

The controller 350 may additionally perform a dense reconstruction analysis operation based on the result of the rough reconstruction analysis in parallel with the rough reconstruction analysis operation, and adjust the rough wave radiation parameter according to the dense reconstruction analysis operation. The controller 350 may output the high-power wave energy based on the adjusted wave radiation parameter and adjust the wave radiation plan, thereby performing a more efficient and highly reliable treatment operation.

If the accumulated procedure is completed by the program, the controller 350 may evaluate the procedure to be performed, in operation 460. When the evaluation is completed, the automatically operable wave energy radiation procedure operation may be terminated.

The components described in the example embodiments may be implemented by hardware components including, for example, at least one digital signal processor (DSP), a processor, a controller, an application-specific integrated circuit (ASIC), a programmable logic element, such as a field programmable gate array (FPGA), other electronic devices, or combinations thereof. At least some of the functions or the processes described in the example embodiments may be implemented by software, and the software may be recorded on a recording medium. The components, the functions, and the processes described in the example embodiments may be implemented by a combination of hardware and software.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter. The above-described devices may be configured to act as one or more software modules in order to perform the operations of the above-described example embodiments, or vice versa.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A method of radiating wave energy available for unmanned automatic operation, the method comprising:
    obtaining a dielectric characteristic of an object by performing a reconstruction calculation based on a scattered signal that is scattered from the object and pre-measured information on the object;
    determining a wave radiation parameter for adjusting energy of a wave to be radiated to a lesion of the object by performing a characteristic analysis operation based on the dielectric characteristic; and
    determining the energy of the wave to be high-power energy based on the wave radiation parameter;
    radiating the wave whose energy is adjusted to the high-power energy to the lesion based on the wave radiation parameter.

2. The method of claim 1, wherein the dielectric characteristic comprises a first dielectric characteristic indicating rough information on an external figure and musculoskeletal system of the object and a second dielectric characteristic indicating detailed information on internal tissues of the object.

3. The method of claim 2, wherein the first dielectric characteristic comprises a rough dielectric characteristic of the object, and the rough dielectric characteristic of the object is related to a shape and size of the external figure of the object and the musculoskeletal system including muscles and bones of the object.

4. The method of claim 2, wherein the second dielectric characteristic comprises a detailed dielectric characteristic of the object, and the detailed dielectric characteristic is related to a distribution of internal muscles, fat, nerves, and vessels of the object, and a structure and positions of a skeleton and bones.

5. The method of claim 2, wherein the obtaining comprises:
    obtaining the scattered signal that is scattered from the object by radiating a wave of low-power energy to the object;
    obtaining the first dielectric characteristic based on the scattered signal and the pre-measured information; and
    obtaining the second dielectric characteristic based on the pre-measured information and the first dielectric characteristic.

6. The method of claim 2, wherein the determining of the wave radiation parameter comprises determining a channel-wise wave radiation parameter for the wave based on the first dielectric characteristic and the second dielectric characteristic.

7. The method of claim 6, wherein the determining of the energy of the wave to be high-power energy comprises:
    outputting a wave of low-power energy based on the channel-wise wave radiation parameter;
    amplifying the wave of the low-power energy to a wave of the high-power energy; and
    determining the wave of the high-power energy as the wave to be radiated to the lesion.

8. The method of claim 1, wherein the pre-measured information is a site of the lesion, a position of the lesion, a shape, size, and diameter with respect to an external figure of the object, a distribution of internal muscles of the object, and anatomical information on a skeleton and bone structure.

9. The method of claim 1, wherein the radiating comprises:
    determining a number of wave radiation channels through which the wave is to be radiated; and
    radiating the wave whose energy is adjusted to the high-power energy based on the determined number of wave radiation channels.

10. An apparatus for radiating wave energy available for unmanned automatic operation, the apparatus comprising:
    an antenna; and
    a controller configured to obtain a dielectric characteristic of an object by performing a reconstruction calculation based on a scattered signal that is scattered through the antenna from the object and pre-measured information on the object, to determine a wave radiation parameter for adjusting energy of a wave to be radiated to a lesion of the object by performing a characteristic analysis operation based on the dielectric characteristic, and to determine the energy of the wave to be high-power energy based on the wave radiation parameter.

11. The apparatus of claim 10, wherein the controller is further configured to radiate the wave whose energy is adjusted to the high-power energy to the lesion based on the wave radiation parameter.

12. The apparatus of claim 10, wherein the dielectric characteristic comprises a first dielectric characteristic indicating rough information on an external figure and musculoskeletal system of the object and a second dielectric characteristic indicating detailed information on internal tissues of the object.

13. The apparatus of claim 12, wherein the first dielectric characteristic is a rough dielectric characteristic related to a shape and size of the external figure of the object and the musculoskeletal system including muscles and bones of the object.

14. The apparatus of claim 12, wherein the second dielectric characteristic is a detailed dielectric characteristic related to a distribution of internal muscles, fat, nerves, and vessels of the object, and a structure and positions of a skeleton and bones.

15. The apparatus of claim 12, wherein the controller is further configured to obtain the scattered signal that is scattered from the object by radiating a wave of low-power energy to the object, to obtain the first dielectric characteristic based on the scattered signal and the pre-measured information, and to obtain the second dielectric characteristic based on the pre-measured information and the first dielectric characteristic.

16. The apparatus of claim 12, wherein the controller is further configured to determine a channel-wise wave radiation parameter for the wave based on the first dielectric characteristic and the second dielectric characteristic.

17. The apparatus of claim 16, wherein the controller is further configured to output a wave of low-power energy based on the channel-wise wave radiation parameter, to amplify the wave of the low-power energy to a wave of the high-power energy, and to determine the wave of the high-power energy as the wave to be radiated to the lesion.

18. The apparatus of claim 10, wherein the pre-measured information is a site of the lesion, a position of the lesion, a shape, size, and diameter with respect to an external figure of the object, a distribution of internal muscles of the object, and anatomical information on a skeleton and bone structure.

19. The apparatus of claim 11, wherein the controller is further configured to determine a number of wave radiation channels through which the wave is to be radiated, and to radiate the wave whose energy is adjusted to the high-power energy based on the determined number of wave radiation channels.

* * * * *